(12) United States Patent
Krohn et al.

(10) Patent No.: US 8,264,129 B2
(45) Date of Patent: Sep. 11, 2012

(54) DEVICE AND SYSTEM FOR MEASURING MATERIAL THICKNESS

(75) Inventors: Matthew Krohn, Lewistown, PA (US); Paul Aloysius Meyer, McVeytown, PA (US); James Norman Barshinger, Niskayuna, NY (US); Ying Fan, Niskayuna, NY (US); Fred Matthews, Lewistown, PA (US); Nathan Smith, Lewistown, PA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/840,485

(22) Filed: Jul. 21, 2010

(65) Prior Publication Data

US 2012/0019105 A1  Jan. 26, 2012

(51) Int. Cl.
*H01L 41/047* (2006.01)
(52) U.S. Cl. ......... 310/365; 310/322; 310/363; 310/800
(58) Field of Classification Search .................. 310/322, 310/344, 363, 365, 800
See application file for complete search history.

(56) References Cited

U.S. PATENT DOCUMENTS

| | | | |
|---|---|---|---|
| 4,926,875 A | 5/1990 | Rabinovitz et al. | |
| 5,262,696 A * | 11/1993 | Culp | 310/328 |
| 5,325,012 A * | 6/1994 | Sato et al. | 310/364 |
| 5,327,895 A | 7/1994 | Hashimoto et al. | |
| 5,548,179 A * | 8/1996 | Kaida | 310/367 |
| 5,834,877 A * | 11/1998 | Buisker et al. | 310/322 |
| 5,923,115 A | 7/1999 | Mohr, III et al. | |
| 6,110,314 A | 8/2000 | Nix et al. | |
| 6,467,140 B2 | 10/2002 | Gururaja | |
| 6,490,228 B2 | 12/2002 | Killam | |
| 6,538,363 B2 | 3/2003 | Nagahara et al. | |
| 6,640,634 B2 | 11/2003 | Hashimoto et al. | |
| 6,789,427 B2 | 9/2004 | Batzinger et al. | |
| 6,822,376 B2 | 11/2004 | Baumgartner | |
| 6,915,547 B2 * | 7/2005 | Takeuchi et al. | 29/25.35 |
| 6,925,869 B2 | 8/2005 | Senibi et al. | |

(Continued)

FOREIGN PATENT DOCUMENTS

JP  2008-173790 A  * 7/2008

(Continued)

OTHER PUBLICATIONS

Mills et al., "Multi-layered PZT/polymer composites to increase signal-to-noise ratio and resolution for medical ultrasound transducers", IEEE Transactions on Ultrasonics, Ferroelectrics and Frequency Control , Jul. 1999, pp. 961-971, vol. 46—Issue No. 4.

*Primary Examiner* — Thomas Dougherty
(74) *Attorney, Agent, or Firm* — Global Patent Operation; Mark A. Conklin

(57) ABSTRACT

A piezoelectric sensing device is described for measuring material thickness of target such as pipes, tubes, and other conduits that carry fluids. The piezoelectric sensing device comprises a substrate such as a flexible circuit material, a piezoceramic element, and a solder layer disposed therebetween. These features are arranged in manner that provides a low-profile measurement device suitable for high-temperature applications such as those applications in which the temperature exceeds 120° C. Embodiments of the piezoelectric sensing device can be configured for use as stand-alone units separately located on the target or for use as a string of sensing elements coupled together by way of the flexible circuit material.

16 Claims, 6 Drawing Sheets

U.S. PATENT DOCUMENTS

| | | |
|---|---|---|
| 7,017,245 B2 | 3/2006 | Baumgartner et al. |
| 7,082,655 B2 | 8/2006 | Yetter et al. |
| 7,148,608 B2 | 12/2006 | Baumgartner et al. |
| 7,156,938 B2 | 1/2007 | Baumgartner et al. |
| 7,291,110 B2 | 11/2007 | Sahatjian |
| 7,293,461 B1 | 11/2007 | Girndt |
| 7,322,243 B2 | 1/2008 | Liu et al. |
| 7,573,181 B2 | 8/2009 | Rhim et al. |
| 7,687,976 B2 | 3/2010 | Haider et al. |
| 7,696,671 B2 | 4/2010 | Sawada et al. |
| 2002/0051848 A1* | 5/2002 | Li .................. 427/376.6 |
| 2006/0154398 A1 | 7/2006 | Qing et al. |
| 2007/0167765 A1* | 7/2007 | Unger et al. ............ 600/437 |
| 2007/0182594 A1* | 8/2007 | Face et al. ................ 341/20 |
| 2009/0039738 A1* | 2/2009 | Angelsen et al. ......... 310/364 |

FOREIGN PATENT DOCUMENTS

| | | |
|---|---|---|
| WO | 2006083245 A1 | 8/2006 |

* cited by examiner

US 8,264,129 B2

DEVICE AND SYSTEM FOR MEASURING MATERIAL THICKNESS

BACKGROUND OF THE INVENTION

The subject matter disclosed herein relates to measuring material thickness using ultrasonic transducers and in one embodiment to a piezoelectric sensing device that comprises a flexible circuit material and a piezoelectric ceramic.

Several industries (e.g., oil and gas, refinery, chemical, power generation) require the transport of fluid (e.g., liquids or gases) through pipes. Nondestructive testing systems can be placed on the outer surface of these pipes to monitor corrosion/erosion of the pipes, including corrosion/erosion on the interior of pipe walls. These systems are usually implemented as part of manual inspection over the course of time, wherein the pipe wall thickness and changes in the thickness are monitored over time. In some cases, the probe or other nondestructive testing device is permanently coupled to the outer surface of the pipe to continuously monitor corrosion/erosion at that location to determine pipe corrosion/erosion rates and to determine whether that pipe location is in need of preventative maintenance to prevent a pipe failure.

One example of a nondestructive testing system used to monitor corrosion/erosion of a pipe is an ultrasonic testing system. When conducting ultrasonic testing of a pipe, an ultrasonic pulse is emitted from a probe coupled to the outer surface of the pipe and passed through the pipe wall. As the ultrasonic pulse passes into and through the pipe wall, various pulse reflections called echoes are reflected back to the probe as the pulse interacts with the outer surface of the pipe, internal structures within the pipe wall, and with the back wall of the pipe wall. The echo signals can be displayed on a screen with echo amplitudes appearing as vertical traces and time of flight or distance as horizontal traces. By tracking the time difference between the transmission of the ultrasonic pulse and the receipt of the echoes, various characteristics of the pipe can be determined, including pipe wall thickness. If the thickness of the pipe wall at the location of the ultrasonic testing system decreases over time (e.g., as would be shown be a reduction in the time of flight of the back wall echo), this can be an indication of corrosion/erosion.

Various factors influence the configuration of devices and in particular the materials for use in these non-destructive testing systems. Operating conditions such as the operating temperature in some applications, for example, can exceed the temperature thresholds of materials such as copolymers of polyvinylidene fluoride (PVDF) (e.g., P(VDF-TrFE)). Processing conditions including temperatures related to certain processing steps during manufacture are also limiting. Performance factors such as accuracy and sensitivity to small defects and to small changes in material thickness are other factors that preclude the use of particular materials and combinations thereof. However, while improved performance can be achieved using certain configurations of materials, these configurations often result in physical characteristics (e.g., height profile) that limit the applicability of the resultant devices.

It would therefore be advantageous to provide a device suited for ultrasonic testing and measurement of material thickness, with improved performance and physical features but that is also configured for high operating temperatures and high process temperatures.

BRIEF DESCRIPTION OF THE INVENTION

In one embodiment a piezoelectric sensing device comprises a substrate, a solder layer disposed on the substrate, and a piezoelectric element coupled to the substrate via the solder layer, the piezoelectric element comprising a ceramic. In one example of the piezoelectric sensing device, the substrate, the solder layer, and the piezoelectric element are arranged as a layered structure that has a profile height that does not exceed 3 mm. In one example o the piezoelectric sensing device, the substrate comprises a material that is compatible with operating temperatures in excess of 120° C.

In another embodiment a measurement system for measuring material thickness of a target. The measurement system comprises a substrate comprising a flexible circuit material having an area with an electrode with a t-shaped geometry. The measurement system also comprises a solder layer disposed on the electrode and a piezoelectric element disposed on the solder layer. The piezoelectric element comprising a ceramic body having a first electrode, a second electrode, and a wrap tab that is coupled to each of the first electrode and the second electrode. The measurement system further comprises a connection for conducting inputs and outputs to and from the piezoelectric element. In one example of the measurement system, the flexible circuit material, the solder layer, and the piezoelectric element are arranged as a layered structure that has a profile height that does not exceed 3 mm.

In yet another embodiment an apparatus for monitoring material thickness of a target. The apparatus comprises a transducer array secured to the target and instrumentation coupled to the transducer array. In one example of the apparatus, the transducer array comprises a piezoelectric sensing device. In one example of the apparatus, the piezoelectric sensing device comprises a layered structure that has a flexible circuit material, a solder layer, and a ceramic body coupled to the flexible circuit material via the solder layer. In one example of the apparatus, the layered structure has a profile height that does not exceed 3 mm.

BRIEF DESCRIPTION OF THE DRAWINGS

So that the manner in which the features of the invention can be understood, a detailed description the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of invention. Thus, for further understanding of the invention, reference can be made to the following detailed description, read in connection with the drawings in which.

DETAILED DESCRIPTION OF THE INVENTION

Figure 1:
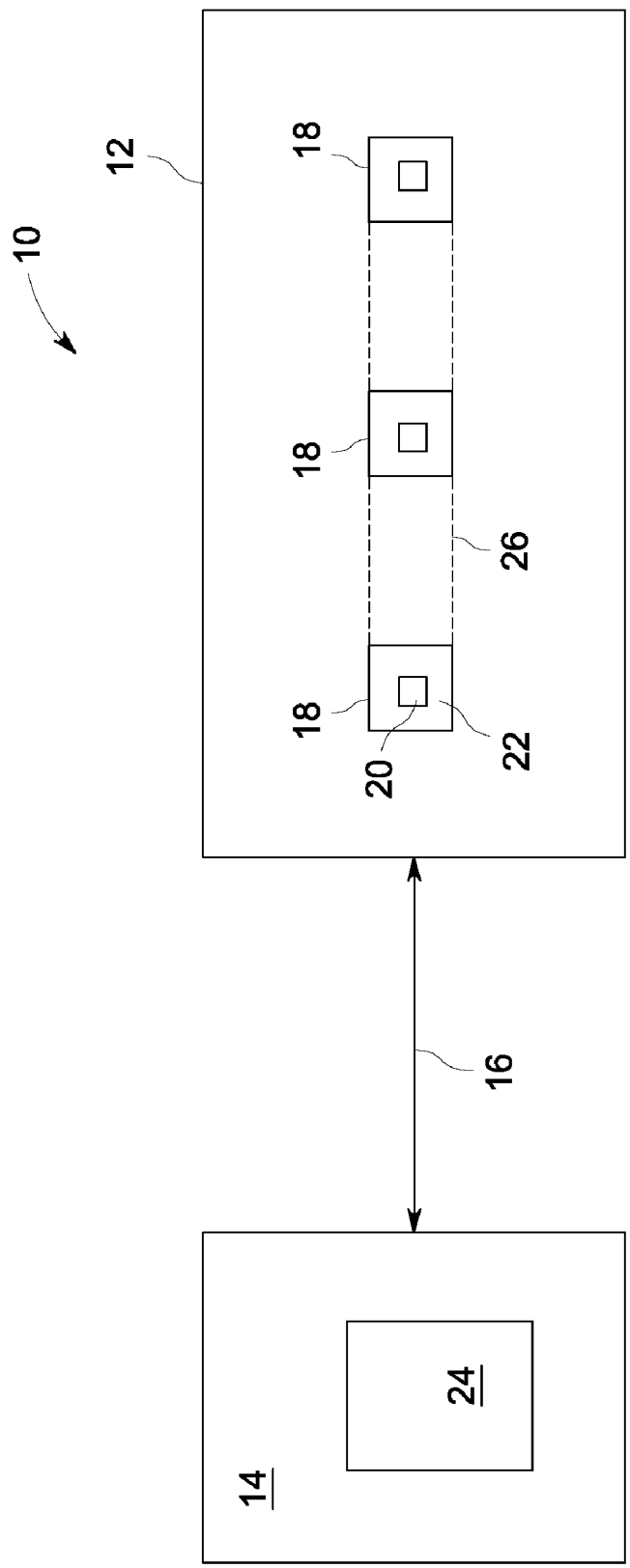
FIG. 1 is a schematic diagram of an exemplary embodiment of a measurement system.

Referring now to the figures, there is illustrated in FIG. 1 an exemplary embodiment of a measurement system 10 with improved sensitivity and construction, the latter of which is beneficial for implementation of the measurement system 10 at operating temperatures greater than, e.g., 120° C., and in areas where access by other measurement systems is limited. The measurement system 10 can comprise a transducer array 12 and instrumentation 14, which is operatively coupled to the transducer array 12 via a connection 16. The transducer array 12 can comprise one or more sensing elements 18, each of the sensing elements 18 having a piezoelectric element 20 coupled to a substrate 22.

Transducer array 12 can be disposed on a target, such as a pipe, a tube, and related conduits that can be subject to corrosion and erosion by way of the fluid that is transported therein. The disposition of the transducer array 12 permits ultrasonic signals generated by the piezoelectric element 20 to impinge on the material of the target. These ultrasonic signals are reflected such as by surfaces of the material, wherein the reflected signals are detected by the piezoelectric element 20.

In one embodiment, instrumentation 14 can include an ultrasonic test unit 24 that generates waveform pulses (generally, "inputs"), which are applied to the piezoelectric element 20 via the connection 16. The waveform pulses cause a mechanical change (e.g., a dimensional change) in the piezoelectric element 20. This change can cause an acoustic wave, which is transmitted through the material of the target. Conversely, the piezoelectric element 20 generates a voltage difference when acoustic waves reflected from the material under inspection contact the surface of the piezoelectric element 20. This voltage difference is detected as receive signals (generally, "outputs") by the ultrasonic test unit 24 or other signal processing electronics.

The ultrasonic test unit 24 can include various control means, which are useful to determine the amplitude, timing, and transmit sequence of the waveform pulse generated by the piezoelectric element 20. The waveform pulse is generally in the frequency range of about 5 MHz to about 20 MHz. By tracking the difference between the transmission of the waveform pulse and the receipt of the received signal and measuring the amplitude of the reflected wave, various characteristics of the material can be determined. In one example, the thickness of the material of the target, as well as any corresponding changes in the thickness, can be determined using time-of-flight analysis, the subject matter of which will be recognized by those artisans having skill in the transducer and related arts.

In one embodiment, the sensing elements 18 are separately arranged and are constructed as individual sensing units. Communication between these individual units and the ultrasonic test unit 24 is facilitated by the connection 16, and in one construction the connection 16 has a plurality of cables (not shown). These cables are coupled to each of the sensing elements 18. Exemplary cables can include coaxial cables and optical fibers, as well as single and plural strands of copper and/or related materials that can conduct the inputs and outputs (e.g., the waveform pulses and the received signals) to and from the piezoelectric element 20 as contemplated herein.

In another embodiment, the sensing elements 18 are arranged on a common substrate, generally demarcated in the present example with the numeral 26. This arrangement is defined by one or more of the piezoelectric elements 20 being disposed on the common substrate 26. The piezoelectric element 20 of the sensing elements 18 can be spaced apart from one another along for example a strip of material, and as discussed in one or more embodiments below, this material can comprise a flexible circuit material that can conform to the shape of the target. In one example, conductors are incorporated in the flexible circuit material, with each conductor terminating at the piezoelectric element 20 and at the end of the common substrate 26. The connection 16 can include one or more connectors (not shown), which are coupled to the conductors, and which can be incorporated or otherwise affixed onto the free end. The connector can be coupled to a mating connector or other device such as a bundle of coaxial cables extending from the ultrasonic test unit 24. This combination can communicate the inputs and outputs between the piezoelectric element 20 and the instrumentation 14.

The number of the sensing elements 18 in the transducer array 12 can vary, and in one construction the number can vary from one to twenty. In one particular example the number is fourteen. An alternative selection of the number can be based on any one or combination of the dimensions of the target under inspection, the preferred spacing of the sensing elements 18 on the target, and the type of defect being detected. When implemented in connection with the common substrate 26, the spacing between the approximate centers of the piezoelectric element 20 can be from about 10 mm to about 100 mm. Moreover, in implementations where the sensing elements 18 are arranged as individualized units, each can be located on the target independently of other ones of the sensing elements 18 of the transducer array 12. Thus the space between adjacent ones of the piezoelectric element 20 and the location of the piezoelectric element 20 relative to features (e.g., edges) of the target can be optimized for each of the sensing elements 18 as desired.

Although the transducer array 12 is depicted as a linear array (e.g., wherein the sensing elements 18 form a single row with one or more columns) other configurations are also envisioned. In one embodiment, the transducer array 12 can include one or more rows and one or more columns of sensing elements 18. In another embodiment, the sensing elements 18 are arranged in formations that are different that arrays of rows and columns. By way of example, one formation for transducer array 12 can comprise a first row of sensing elements 18 and a second row of sensing elements 18, wherein the second row is positioned in perpendicular relation to the first row, thus forming a "t" shape.

Figure 2:
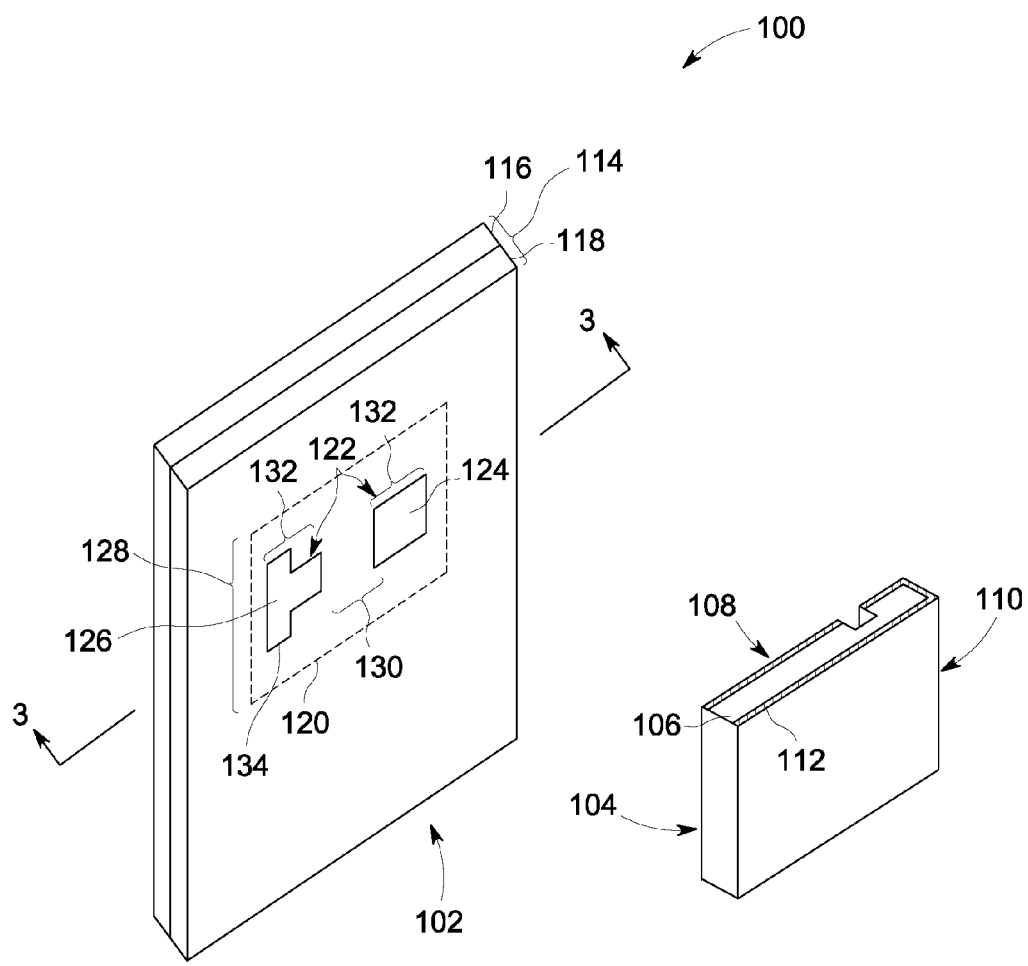
FIG. 2 is an exploded assembly view of an exemplary embodiment of a piezoelectric sensing device.
Figure 3:
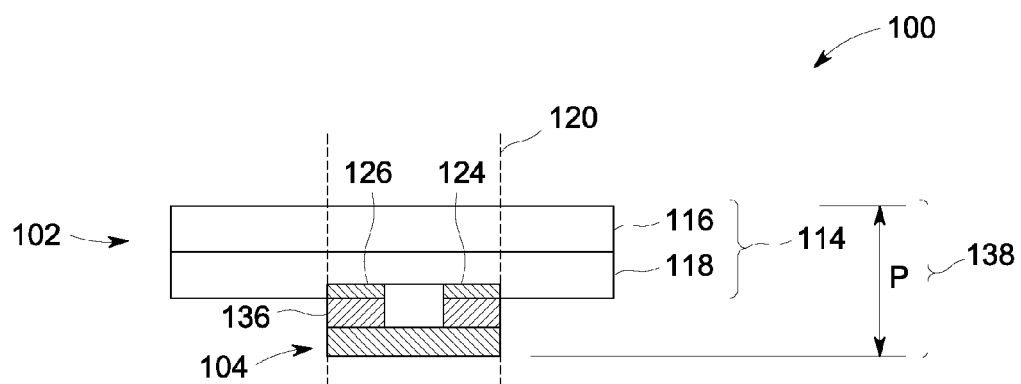
FIG. 3 is a side, cross-section, assembled view of the piezoelectric sensing device of FIG. 2.

Focusing now on the construction of the sensing elements 18, reference can be had to FIGS. 2 and 3. Here there is depicted an exemplary embodiment of a piezoelectric sensing device 100 which can be deployed as one or more of the sensing elements 18 of FIG. 1. In one embodiment, the piezoelectric sensing device 100 can comprise a substrate 102 and a piezoelectric element 104 with a ceramic body 106. The ceramic body 106 can be configured with an electrode 108, a ground 110, and a wrap tab 112 constructed of gold plating or comparable conductive material that is deposited on the ceramic body 106. The substrate 102 can comprise a flexible circuit material 114, shown in this example with a first layer 116 and a second layer 118, and with a receiving area 120 that is configured to receive the piezoelectric element 104. The receiving area 120 can have electrodes 122 for connecting to, e.g., the electrode 108 and the ground 110. The electrodes 122 can include a first or ground electrode 124 and a second or hot electrode 126. The electrodes 122 can conform to an electrode geometry 128 that is defined by an isolation gap 130 between the electrodes 122 and/or a shape geometry 132 as applied to one or both of the electrodes 122. In one example the shape geometry 132 comprises a t-shaped geometry 134 for the hot electrode 126.

In one embodiment, the piezoelectric sensing device 100 may also include a solder layer 136 that comprises one or more materials such as tin, lead, silver, bismuth, and indium. The solder layer 136 is deposited during assembly and is used to couple the piezoelectric element 104 to the receiving area 120 of the substrate 102. When assembled, the combination of the substrate 102, the piezoelectric element 104, and the solder layer 136 are arranged as a layered structure 138 with a profile height P. Embodiments of the piezoelectric sensing device 100 can be configured so that the profile height P does not exceed about 7 mm, and in one example the profile height is from about 0.25 mm to about 1 mm. These values are smaller than conventional devices, which permits use of the piezoelectric sensing device 100 in places that are generally not accessible with measurement devices of conventional construction.

Materials for use in the ceramic body 106 are selected for their properties including for example compatibility with processing conditions during assembly such as the reflow temperatures required to reflow the solder layer 136. These reflow temperatures typically are in excess of 200° C. and in one exemplary process the reflow temperatures is about 220° C. Other properties to consider include, but are not limited to, dielectric constant of the material, wherein the materials that are selected for the ceramic body 106 should have a dielectric constant that renders good electrical impedance matching, while minimizing the overall dimensions of the piezoelectric element 104. These dimensions include, for example, dimensions for the rectangular shape of FIG. 2 of about 3 mm by about 5 mm, although the length and width can vary, respectively, from about 2 mm to about 8 mm. In other examples, the shape of the piezoelectric element 104 can comprise a square, a circle, and/or an ellipse. With reference to the profile height P discussed above, it is further contemplated that piezoelectric element 104 is formed with an overall thickness from about 0.1 mm to about 1 mm.

In one embodiment, it may be desirable to use piezoelectric ceramics such as Navy Type II materials and related ceramics (e.g., lead zirconium titanate piezoelectric), although other materials having similar properties and composition are likewise contemplated and may be used. For purposes of constructing the ceramic body 106 (and the piezoelectric element 104 in general), in one example a brick of Navy Type II material can be diced into plates having a thickness on the order of 0.6 mm. These plates can be finished by way of finish grinding operations so that the thickness of the resulting plates is about 0.2 mm. Linear grinding, lapping, and back grinding are all acceptable finish grinding operations. The plates can thereafter be cut into strips with a width of about 9 mm and the electrodes can be formed, poled, and tested. Plating operations such as sputtering can be used to deposit the gold (Au) plating and the finished plates can be diced to form the individual piezoelectric elements (e.g., the piezoelectric element 104). In one example, a single brick of Navy Type II material can yield approximately 2880 of the piezoelectric element 104. It will be appreciated that the electrodes 122 can be formed using certain deposition, etching, sputtering, and related processing techniques and processes recognized within the scope and spirit of the present disclosure.

The layers (e.g., the first layer 116 and the second layer 118) of the flexible circuit material 114 can comprise materials such as a polyamide-based film, as well as other materials and films that comprise one or more of polyester (PET), polyimide (PI), polyethylene napthalate (PEN), and polyetherimide (PEI). The layers can be constructed together to form a laminate that is compatible with the processing conditions, operating temperatures, and physical characteristics (e.g., the profile height P) discussed herein. Conductors such as electrical conductors like metal foil may be included among the layers, or in other examples the conductors can be incorporated amongst the layers such as by using electroplating and related plating and deposition techniques. These conductors can extend to the electrodes 122 as well as to peripheral edges and areas of the substrate 102. This configuration is useful to conduct the pulse and electrical signals to and from the piezoelectric element 104, an example of which was discussed above in connection with the common substrate (e.g., the common substrate 26 of FIG. 1).

Figure 4:
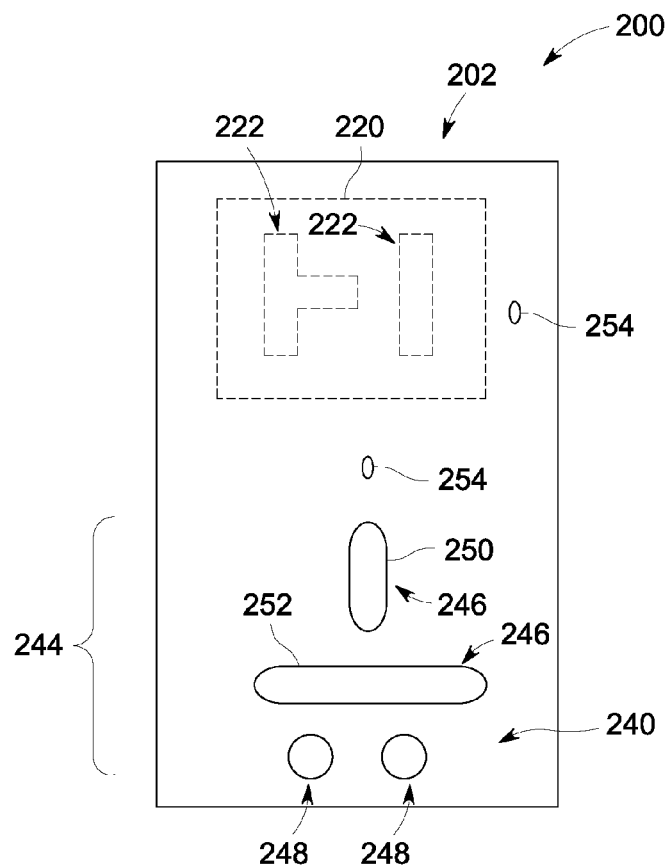
FIG. 4 is a front view of another exemplary embodiment of a piezoelectric sensing device.
Figure 5:
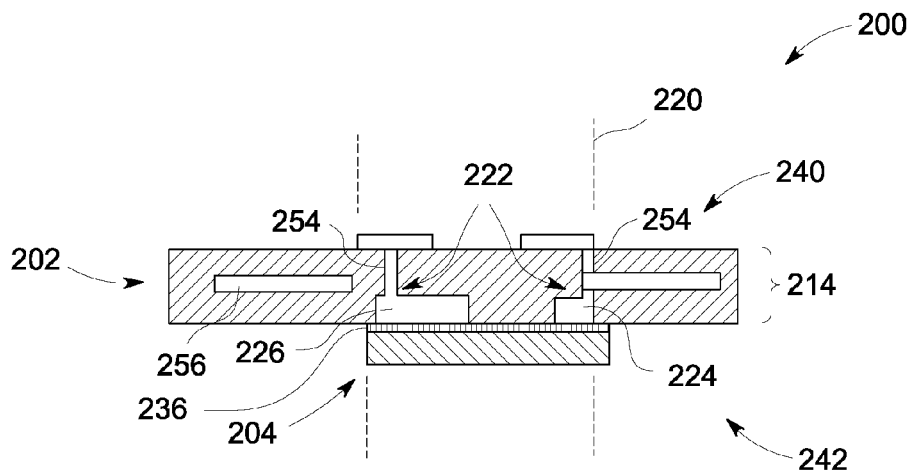
FIG. 5 is a side, cross-section view of the piezoelectric sensing device of FIG. 4.
Figure 6:
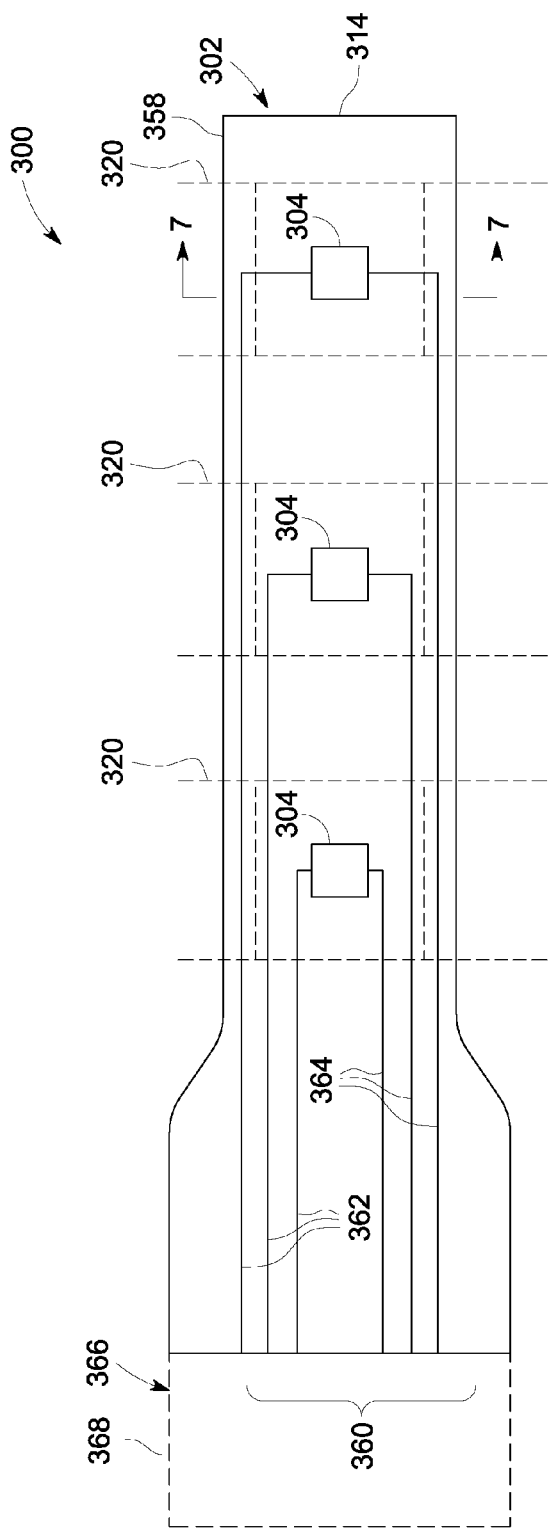
FIG. 6 is a front view of yet another exemplary embodiment of a piezoelectric sensing device.
Figure 7:
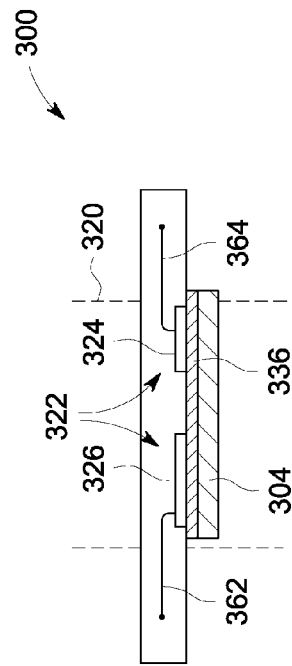
FIG. 7 is a side, cross-section view of the piezoelectric sensing device of FIG. 6.

Referring next to FIGS. 4-7, there is provided exemplary embodiments of a piezoelectric sensing device 200 (FIGS. 4 and 5) and 300 (FIGS. 6 and 7). For purposes of the discussion that follows below, like numerals are used to identify like components as between FIGS. 2-7, except that the numerals are increased by 100 (e.g., 100 is 200 in FIGS. 4 and 5, and 200 is 300 in FIGS. 6 and 7). The piezoelectric sensing devices 200 and 300 are useful for implementation in one or more of the configurations of the transducer array 12 discussed in connection with FIG. 1 above.

The piezoelectric sensing device 200 that is depicted in FIGS. 4 and 5, for example, is suited for use in connection with the configuration of the transducer array 12 (FIG. 1) wherein each of the sensing elements 18 is arranged as individual units. In one embodiment, the piezoelectric sensing device 200 can comprise a substrate 202 and a piezoelectric element 204. The substrate 202 can comprise a flexible circuit material 214 with a receiving area 220 in which is positioned the piezoelectric element 204. The receiving area 220 can have electrodes 222 including a ground electrode 224 and a hot electrode 226. A solder layer 236 can be disposed on one or more of the electrodes 222 using screen printing techniques recognized in the art.

The flexible circuit material 214 can comprise a frontside 240 and a backside 242 on which are located the electrodes 222. The piezoelectric sensing device 200 can also comprise one or more cable connections 244 with cable connection pads 246 and strain reliefs 248. The cable connection pads 246 can include a ground pad 250 and a hot pad 252, each being coupled to, respectively, the ground electrode 224 and the hot electrode 226 by way of one or more vias 254. The vias 254 extend through the flexible circuit material 214, thereby coupling the cable connection pads 246 on the frontside 240 to the electrodes 222 on the backside 242. In one example, a ground plane 256 is also incorporated into the flexible circuit material 214. The ground plane 256 is coupled to the ground electrode 224 and the ground pad 250.

The piezoelectric sensing device 300, as depicted in FIGS. 6 and 7, can be implemented when the transducer array 12 (FIG. 1) utilizes a common substrate (e.g., the common substrate 26 (FIG. 1)). In one embodiment, the piezoelectric sensing device 300 can comprise a substrate 302 and a piezoelectric element 304. The substrate 302 can comprise a flexible circuit material 314 with one or more receiving areas 320 configured for receiving the piezoelectric element 304 thereon. The receiving areas 320 can have electrodes 322 including a ground electrode 324 and a hot electrode 326. A solder layer 336 is also included for securing the piezoelectric element 304 to the electrodes 322.

The piezoelectric sensing device 300 can comprise a common substrate 358 in which a plurality of conductors 360 are incorporated. The conductors 360 can include hot conductors 362 and ground conductors 364, each being illustrated as extending from a free end 366 of the common substrate 358. Disposed on the free end 366 is a connector 368 such as a multi-pin connector that is coupled to each of the conductors 360. The connector 368 is likewise configured to couple to a mating connector (not shown) as might be associated with the instrumentation (e.g., instrumentation 14 (FIG. 1)) contemplated herein.

Figure 8:
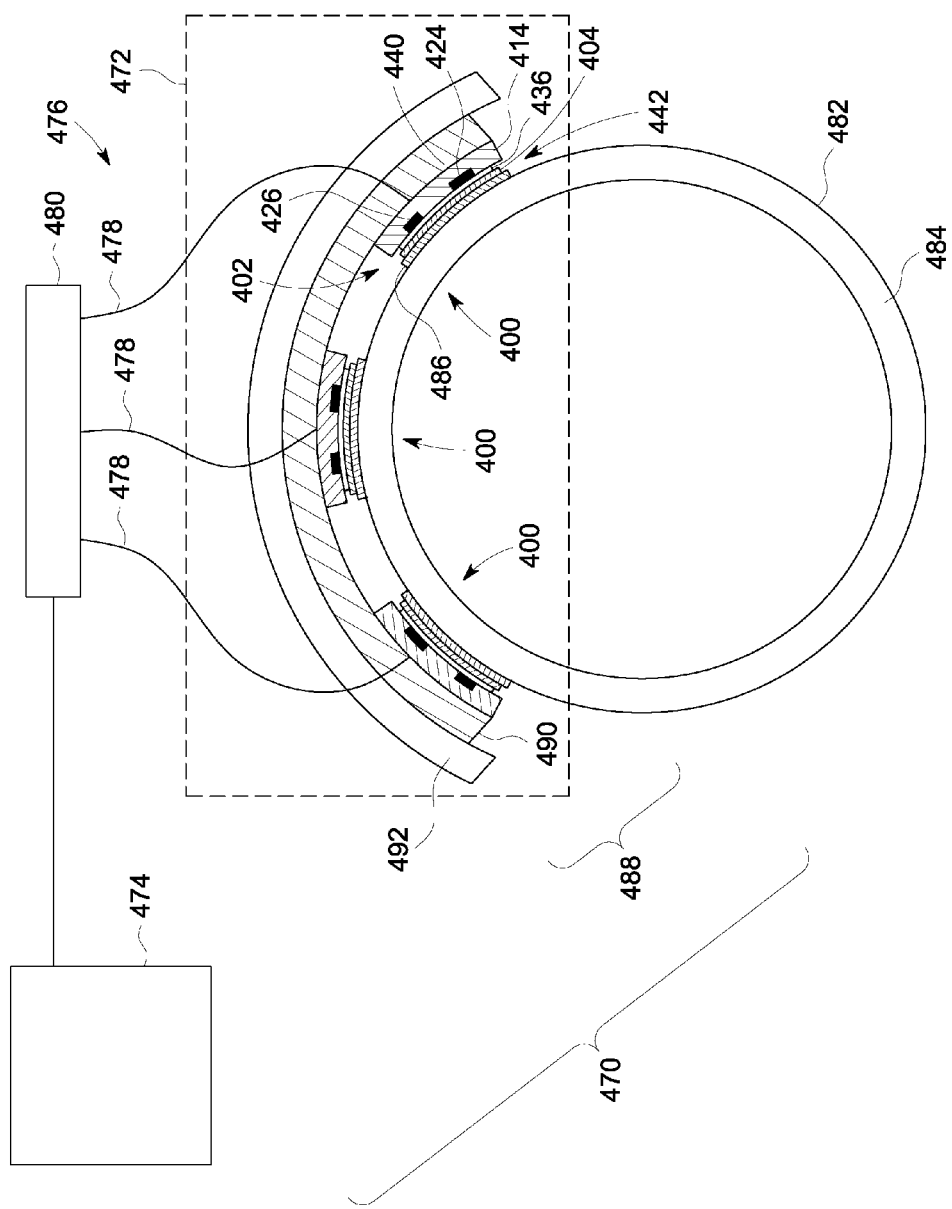
FIG. 8 is a schematic diagram of an implementation of a piezoelectric sensing device such as the piezoelectric sensing devices of FIGS. 2-5.
Figure 9:
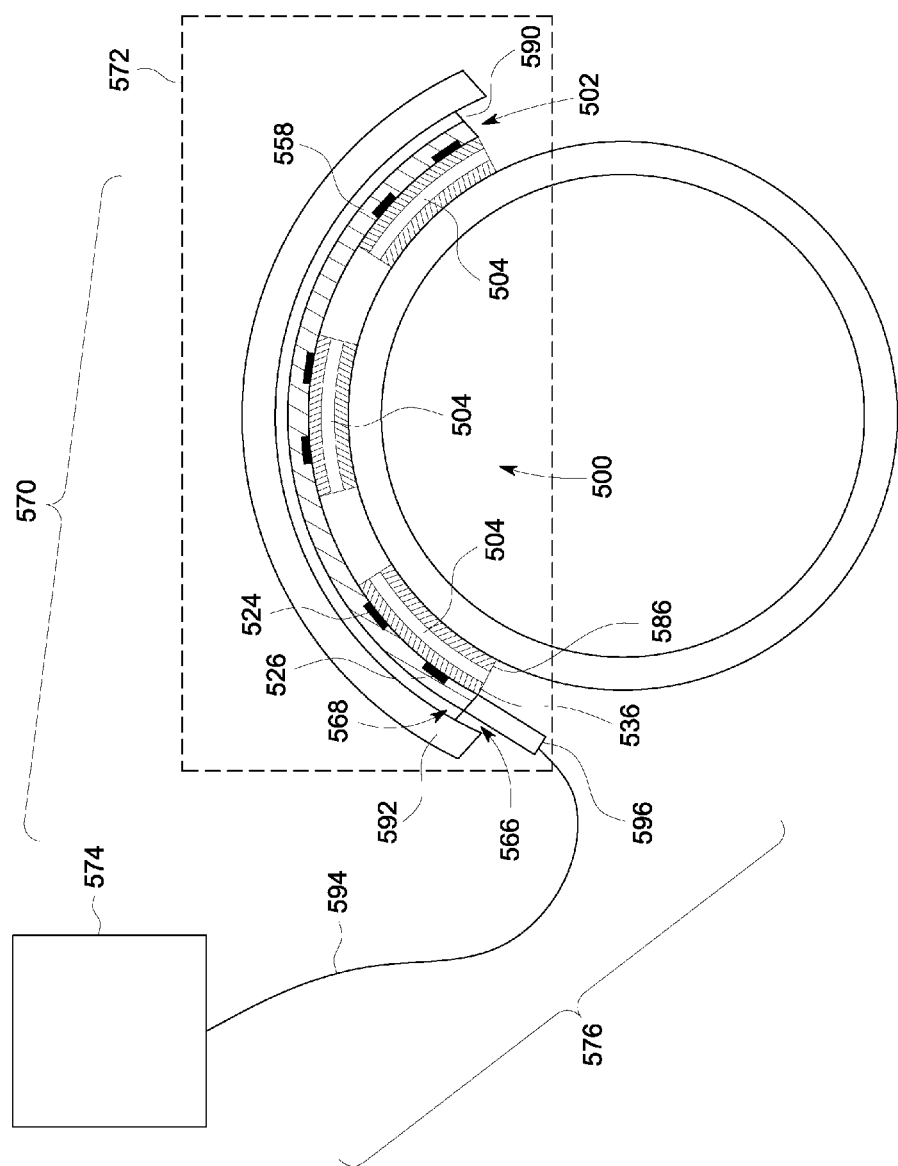
FIG. 9 is a schematic diagram of another implementation of a piezoelectric sensing device such as the piezoelectric sensing devices of FIGS. 2, 3, 6, and 7.

Discussing now the implementation of piezoelectric sensing devices such as the piezoelectric sensing devices 100, 200, and 300 discussed above, reference is now directed to FIGS. 8 and 9. The FIGS. 8 and 9 illustrate, respectively exemplary embodiments of a piezoelectric sensing device 400 and 500, these embodiments being configured for use in measurement systems such as the measurement systems described above and in more detail below. Like numerals are also used to identify like components as between the FIGS. 2-9. However, although some of the features and concepts of the piezoelectric sensing devices of the present disclosure may not be depicted or discussed in connection with FIGS. 8 and 9, it is contemplated that such features and concepts are applicable to the piezoelectric sensing devices 400 and 500 as well as embodiments and derivation thereof.

There is depicted in FIG. 8, for example, a plurality of piezoelectric sensing devices 400, each of which can comprise a substrate 402 and a piezoelectric element 404. The substrate 402 can include a flexible circuit material 414 with a ground electrode 424, a hot electrode 426, and a solder layer 436 that is used to secure the piezoelectric element 404 to the substrate 402. The flexible circuit material 414 includes a frontside 440 and a backside 442. In one embodiment, the piezoelectric sensing devices 400 are implemented as part of a measurement system 470, which can comprise a transducer array 472, instrumentation 474, and a connection 476 such as one or more cables 478 that are coupled to the piezoelectric element 404. The measurement system 470 can also comprise a connection terminal 480 to aggregate the cables 478, acting in one example as a central hub for communicating signals to and from the instrumentation 474 and the piezoelectric sensing devices 400 of the transducer array 472.

In one embodiment, the piezoelectric sensing devices 400 are secured to a surface 482 of a target 484 using a couplant 486 such as an adhesive that is disposed on the backside 442 of the substrate 402. To further ensure proper functioning and coupling of the piezoelectric sensing devices 400 to the surface 482, one or more outer structures 488 can be utilized such as a protective layer 490 and a fastening mechanism 492. These outer structures 488 can be incorporated as part of the piezoelectric sensing devices 400 or in one embodiment the outer structures 488 comprise one or more pieces separate from the piezoelectric sensing devices 400. Assembly of the pieces of the outer structures 488 can occur at the time of implementation and installation of piezoelectric sensing devices 400 and the measurement system 470 generally.

The couplant 486 can be disposed on surfaces of the substrate 402, as depicted in FIG. 8, as well as on the piezoelectric element 404. Care should be taken during application to avoid degradation of the performance of the piezoelectric element 404. In addition to performance characteristics, it may be desirable that materials for use as the couplant 486 are compatible with the material characteristics of the substrate 402 and the target 484. In one example, adhesives such as acrylic adhesives can be applied at as a layer with a nominal initial thickness of about 1 mm. Other adhesives and related materials that may be likewise acceptable include, but are not limited to, cyanocrylates, epoxies, solvent-based adhesives, and cold-flow adhesives, as well as combinations and derivations thereof.

The protective layer 490 is used to prevent damage to the underlying structure, e.g., the piezoelectric sensing devices 400. Materials can likewise have electrically insulating properties thus providing protection from the outer environment as well as preventing arcing, shorting, and other electrical-induced failures that can occur. Exemplary materials for use as the protective layer 490 can include silicon, nylon, neoprene, polymeric materials, and combinations and derivations thereof.

The fastening mechanism 492 can be in the form of the band-like structure illustrated in FIG. 8. When the target 484 is a pipe or other circumferential device, such structures can be affixed about the circumference. These structures can incorporate secondary fastening and tightening features that reduce the diameter of the band about the pipe, thereby applying a force onto the piezoelectric sensing devices 400. For other configurations of the target 484, such as for targets with flat or irregular constructions, the fastening mechanism 492 may be configured with devices that are designed for the specific configuration of the target 484. These devices may include magnets and magnetized implements that can cause to be applied to force onto the piezoelectric sensing devices 400.

Referring now to FIG. 9, it is seen that the piezoelectric sensing device 500 can comprise a substrate 502 and a piezoelectric element 504. The substrate 502 can comprise a ground electrode 524 and a hot electrode 526, and a solder layer 536 is included as contemplated herein. The substrate 502 is arranged as a common substrate 558 with a free end 566 on which is disposed a connector 568. The piezoelectric sensing device 500 is part of a measurement system 570, which can comprise a transducer array 572, instrumentation 574, and a connection 576 coupled therebetween. To secure the piezoelectric sensing device 500, a couplant 586 is used and further protection is afforded by a protective layer 590 and a fastening mechanism 592. In one embodiment, the connection 576 can comprise a single cable 594 that is coupled to the connector 568 and to the instrumentation 574. The single cable 594 can comprise, for example, a mating connector 596 that is configured to mate with the connector 568.

This written description uses examples to disclose embodiments of the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A piezoelectric sensing device comprising:
a substrate;
a solder layer disposed on the substrate;
a piezoelectric element coupled to the substrate via the solder layer, the piezoelectric element comprising a ceramic; and a wrap tab comprising conductive material disposed on three surfaces of the piezoelectric element and covering the extent of at least one of the three surfaces of the piezoelectric element, wherein the substrate, the solder layer, and the piezoelectric element are arranged as a layered structure that has a profile height that does not exceed 3 mm, and wherein the substrate comprises a material that is compatible with operating temperatures in excess of 120° C.

2. A piezoelectric sensing device according to claim 1 wherein the substrate and the ceramic are compatible with reflow temperatures used to process the solder layer.

3. A piezoelectric sensing device according to claim 1 wherein the ceramic comprises a Navy Type II material.

4. A piezoelectric sensing device according to claim 1 wherein the substrate comprises a polyamide-based film.

5. A piezoelectric sensing device, comprising:
a substrate;
a solder layer disposed on the substrate; and
a piezoelectric element coupled to the substrate via the solder layer, the piezoelectric element comprising a ceramic;
wherein the substrate, the solder layer, and the piezoelectric element are arranged as a layered structure that has a profile height that does not exceed 3 mm,
wherein the substrate comprises a material that is compatible with operating temperatures in excess of 120° C. and
wherein the substrate comprises an area with an electrode that has a t-shaped geometry, and wherein the piezoelectric element is secured to the area with the solder layer.

6. A piezoelectric sensing device according to claim 5 further comprising a wrap tab disposed around at least a portion of the piezoelectric element.

7. A piezoelectric sensing device according to claim 5 further comprising a gold plating disposed on the piezoelectric element.

8. A piezoelectric sensing device according to claim 5 further comprising one or more cable connections disposed on a frontside of the substrate, wherein the piezoelectric element is disposed on a backside of the substrate, and wherein the one or more cable connections are configured to conduct inputs and outputs to and from the piezoelectric element and one or more cables secured to the one or more cable connections.

9. A piezoelectric sensing device according to claim 5 further comprising a conductor incorporated into the substrate, wherein the conductor is coupled to the piezoelectric element and to a free end of the substrate.

10. A piezoelectric sensing device according to claim 9 further comprising a connector coupled to the conductor at the free end, wherein the connector communicates inputs and outputs to and from the piezoelectric element.

11. A measurement system for measuring material thickness of a target, said measurement system comprising:
a substrate comprising a flexible circuit material having an area with an electrode with a t-shaped geometry;
a solder layer disposed on the electrode;
a piezoelectric element disposed on the solder layer, the piezoelectric element comprising a ceramic body having a first electrode, a second electrode, and a wrap tab that is coupled to each of the first electrode and the second electrode; and
a connection for conducting inputs and outputs to and from the piezoelectric element, wherein the flexible circuit material, the solder layer, and the piezoelectric element are arranged as a layered structure that has a profile height that does not exceed 3 mm.

12. A measurement system according to claim 11 further comprising a couplant disposed on one or more of the flexible circuit material and the ceramic body, wherein the couplant adheres to a surface of the target.

13. A measurement system according to claim 11 further comprising a protective layer disposed on the flexible circuit material.

14. A measurement system according to claim 11 wherein the flexible circuit material comprises a first layer, a second layer, and a conductor disposed between the first layer and the second layer, and wherein the connection comprises a connector coupled to the conductor and disposed on a free end of the flexible circuit material.

15. A measurement system according to claim 11 wherein the connection comprises a cable secured to one or more cable connections incorporated into the flexible circuit material.

16. A measurement system according to claim 11 further comprising instrumentation coupled to the connection, wherein the instrumentation is configured to transmit inputs to the ceramic body, and wherein the inputs excite the ceramic body.

* * * * *